United States Patent [19]

Deleuil et al.

[11] Patent Number: 5,380,532

[45] Date of Patent: * Jan. 10, 1995

[54] PROCESS FOR THE PREPARATION OF MEDICATION IN THE FORM OF PEARLS

[75] Inventors: Michel Deleuil, Antony; Pierre Labourt-Ibarre, Lyon; Robert Rona, Saint-Germain-en-Laye; Eraclis Statiotis, Villette D'Anthon, all of France

[73] Assignee: Rhone-Poulenc Rorer, S.A., France

[ * ] Notice: The portion of the term of this patent subsequent to Nov. 24, 2009 has been disclaimed.

[21] Appl. No.: 917,569

[22] Filed: Jul. 21, 1992

Related U.S. Application Data

[63] Continuation of Ser. No. 642,947, Jan. 18, 1991, Pat. No. 5,188,838.

[30] Foreign Application Priority Data

Jan. 19, 1990 [FR] France ................................ 90 00623

[51] Int. Cl.⁶ ............................................. A61K 9/48
[52] U.S. Cl. ...................................... 424/451; 424/458; 424/473; 424/490; 424/494; 424/497
[58] Field of Search ............... 23/313 R, 308 R, 293 A; 264/5, 13, 9; 425/6, 8; 71/28; 424/451, 494, 497, 458, 473

[56] References Cited

U.S. PATENT DOCUMENTS

| | | | |
|---|---|---|---|
| 4,035,116 | 7/1977 | O'Brien et al. | 264/5 |
| 4,283,325 | 8/1981 | Berthet | 424/81 |
| 4,313,745 | 2/1982 | Kendall | 264/5 |
| 4,389,356 | 6/1983 | Higgins | 264/9 |
| 4,483,867 | 11/1984 | Svahn | 514/870 |
| 4,525,198 | 6/1985 | Van Hijfte et al. | 71/28 |
| 4,548,818 | 10/1985 | Kjellin | 514/263 |
| 4,627,943 | 12/1986 | Seidler | 264/13 |
| 4,913,865 | 4/1990 | Toyotama | 264/5 |

FOREIGN PATENT DOCUMENTS 2725849  12/1978  Germany .
2725924  12/1978  Germany .

Primary Examiner—Thurman K. Page
Assistant Examiner—William E. Benston, Jr.
Attorney, Agent, or Firm—Morgan & Finnegan

[57] ABSTRACT

Process for the preparation of pearls based on a pharmaceutical active substance exhibiting an indefinite crystallization point.

The said active substance is mixed in molten form with a pharmaceutical excipient promoting the solidification of the active substance, the melt is forced to pass through a nozzle which is subjected to a vibration, the pearls formed are allowed to fall in a tower countercurrentwise to a gas, and the pearls formed are collected in the bottom of the tower.

8 Claims, 2 Drawing Sheets

PROCESS FOR THE PREPARATION OF MEDICATION IN THE FORM OF PEARLS

This is a continuation of co-pending application Ser. No. 07/642,947 filed Jan. 18, 1991, now U.S. Pat. No. 5,188,838.

FIELD OF THE INVENTION

The present invention relates to a new presentation of pharmaceutical active substances in the form of pearls and to the process for their preparation. It relates more particularly to the conversion into pearl form of medicinal active substances which exhibit a supercooling phenomenon.

BACKGROUND OF THE INVENTION

Chemical compounds converted into pearl form are better known in the prior art by the name of "prills". In most cases they relate to inorganic products exhibiting no phenomenon of degradation either by heat or by moisture. The conversion into pearl form is simply carried out for convenience in use, because the pearls have a uniform distribution with regard to the diameter and the shape of the particles.

The manufacture of these pearls is described especially in patents EP 277,508, U.S. Pat. No. 4,525,198, and U.S. Pat No. 4,389,356. Processes for the preparation of these pearls consist, in a first stage, in melting the compound which is to be formulated and then passing it through a die or a perforated plate which is subjected at its base to flows which make it possible to form pearls or beads which fall in a tower countercurrentwise to a gas or to air, thus permitting the solidification of the beads, which do not adhere to the walls of the tower.

This process is widely employed for converting fertilizers (urea, nitrogen compound, phosphorus compound, and the like) because these products can be subjected to a violent heating to make them melt and to a fast cooling to ensure their solidification. In addition, the dimensional uniformity of the pearls (approximately a few millimeters) is not such a draconian condition in the fertilizer industry as in the pharmaceutical industry, where pearl dimensions of the order of a few tens of to a few hundred microns are desired.

When melted, some active substances exhibit so-called "supercooling" phenomena which considerably delay their solidification, even after cooling. The problem which the present invention has attempted to solve is that of converting into bead form those medicinal active substances which exhibit an indefinite crystallization point (or more commonly a supercooling phenomenon) and which therefore do not lend themselves well to the "prilling" technique because they tend to remain in an oily or pasty form well after returning to a temperature below their melting temperature. On passing compounds of this type through a prilling tower it was expected to have a pasty mass at the bottom of the tower or on the walls. The technique which consisted in blowing a jet of very cold air ($-10°$ C. to $-20°$ C.) over the jet of molten substance leaving the nozzle did not enable the problem to be solved. In fact, when supercooled products are brought into contact with an intense cold, the viscosity of the liquid increases considerably and slows down the subsequent crystallization. It was therefore necessary to avoid at all costs introducing a jet of excessively cold air at the exit of the nozzle.

DETAILED DESCRIPTION OF THE INVENTION

Figure 1:
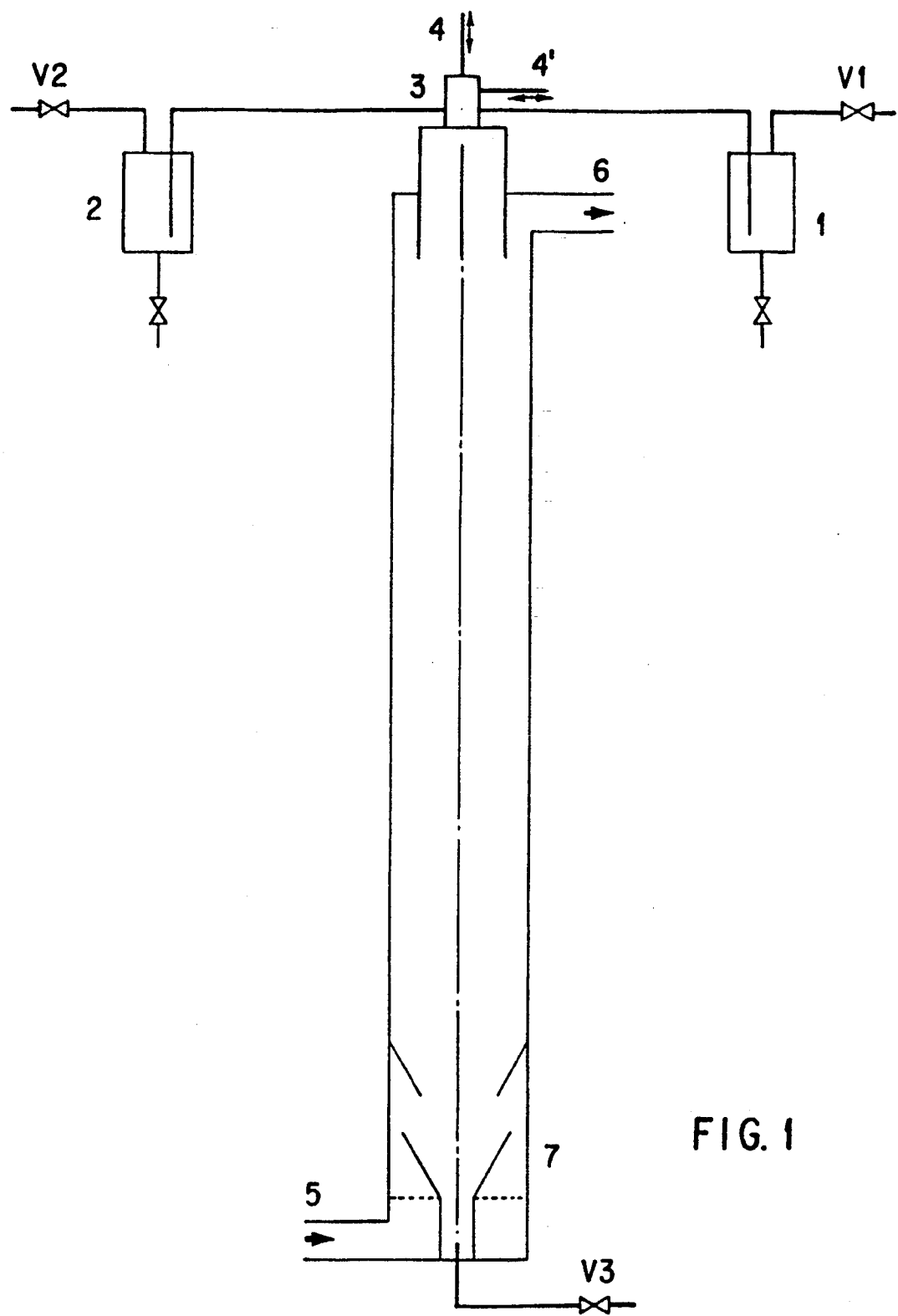
FIG. 1 describes active substance exhibiting supercooling phenomenon.
Figure 2:
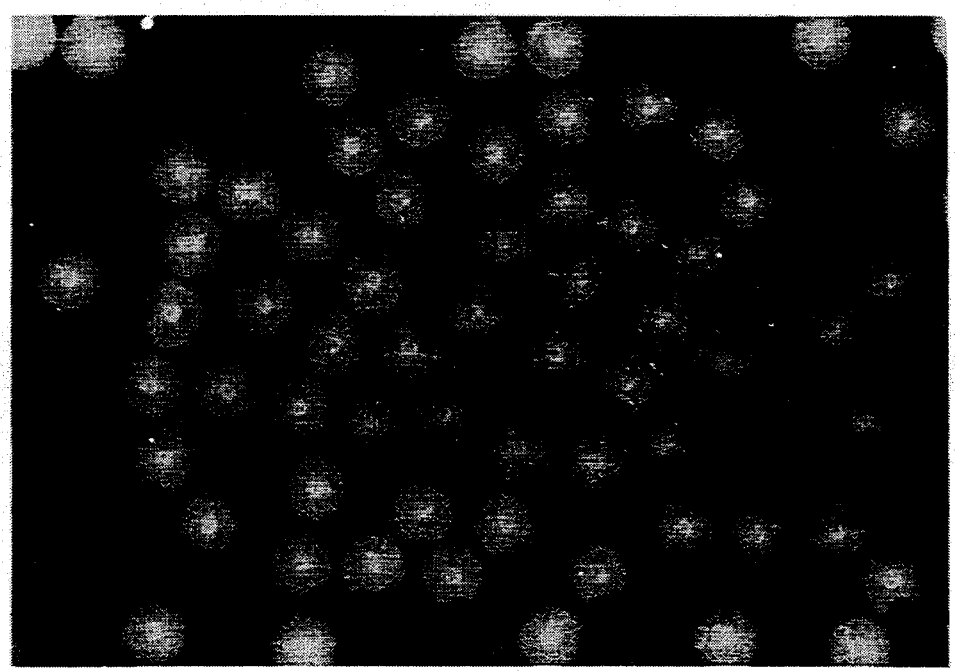
FIG. 2 shows excipient in a container.

The present invention has allowed this problem to be solved without resulting to very intense cooling or to towers of excessively great height.

It consists in converting into pearl form a pharmaceutical active substance exhibiting an indefinite crystallization point, in which the said active substance is mixed with one or more pharmaceutical excipients in molten form, the melt is forced to pass through a nozzle which is subjected to a vibration, the pearls formed are allowed to fall in a tower countercurrentwise to a gas, and the solid pearls are collected in the bottom of the tower.

A fluidized bed which makes it possible to keep permanently fluidized the pearls which have not yet completely solidified is optionally joined onto this prilling tower.

The active substances which have an indefinite solidification point and which therefore exhibit a supercooling phenomenon are chosen especially from:
  2-(3-benzoylphenyl)propionic acid or ketoprofen,
  2-methyl-2-propyl-1,3-propanediol dicarbonate or meprobamate
  2-(4-isobutylphenyl)propionic acid.

The additives which enable the crystallization of the supercooled product to be induced are chosen from the products employed for pharmaceutical use, such as:
  fatty alcohols such as:
    cetyl alcohol,
    stearyl alcohol,
  fatty acids such as:
    stearic acid,
    palmitic acid,
  glycerol esters such as:
    glycerol palmitostearate,
    the glycerol stearate marketed under the mark Precirol,
    the glycerol behenate marketed under the mark Compritol,
  hydrogenated oils such as:
    hydrogenated castor oil marketed under the mark Cutina HR,
  fatty acid salts such as:
    magnesium or calcium stearate,
  polyols such as:
    mannitol,
    sorbitol,
    xylitol,
  waxes such as:
    white wax,
    carnauba wax,
    paraffin wax,
  polyoxyethylene glycols of high molecular weight,
  esterified polyoxyethylenes such as:
    PEG-32 distearate,
    PEG-150 distearate.

Among the active substances exhibiting a supercooling problem, the problem is particularly great in the case of 2-(3-benzoylphenyl)propionic acid. The excipients which can be used to promote the solidification of this compound must obviously be inert towards the latter, thus only the following classes of excipients can be employed:
fatty acids and their salts,
glycerol esters,
hydrogenated oils,
waxes,
esterified polyoxyethylenes.

In the case of 2-(3-benzoylphenyl)propionic acid it is preferred to employ glycerol esters mixed with stearic acid. It is also preferred to employ at least 20% of excipient to formulate up to 80% of active substance and preferably between 30 and 40% of excipient. More particularly, an excipient containing at least 20% of stearic acid is preferred.

To these crystallization additives it is sometimes desirable to add polymers which are soluble or dispersible in the melt, which will permit a completely controlled and adjustable dissolution of the pearls when they are used, such as:
cellulose derivatives (hydroxypropyl cellulose, hydroxypropyl methyl cellulose, hydroxyethyl cellulose, ethyl cellulose, carboxymethyl cellulose),
acrylic resins (marketed under the mark Eudragit),
polyvinyl acetates (marketed under the mark Rhodopas),
polyalkylene (ethylene propylene), polylactic, maleic anhydride and silicone resins.

Some inorganic additives make it possible, with crystallization additives, to accelerate the solidification of the active substances which exhibit this supercooling phenomenon. Examples which may be mentioned are:
silicas,
inorganic oxides such as titanium or iron oxide,
phosphates,
carbonates,
clays,
talc.

To improve the dispersion of the active substance in the crystallization additive it is sometimes useful to add a surface-active agent chosen, for example, from sorbitol esters, the polyoxyethylene polysorbates marketed under the mark Tween, and glycols such as glycerine or propylene glycol.

The process for the preparation of pearls consists in preparing a melt of the active substance(s) with one or more excipients. This melt can be prepared by separately melting the various constituents and then mixing them or by melting the mixture of the constituents, possible insoluble compounds being added at the end of the melting so as to obtain a homogeneous mass.

The nature of the constituents of the melt is chosen by the person skilled in the art, which is considered as a function of the compatibility of the constituents, the viscosity of the mixture of constituents, the nozzle diameter, the hydrophilicity of the active substance, the surface tension of the active substance, the particle size of the insoluble additives, the flow rate of the nozzle, the temperature of the tower, its height and, above all, the size or the desired pearls, the proportion of active substance to be included therein and the desired release time of the active substance.

The in-vitro release and the in-vivo availability of the active substance from these pearls is modified (prolonged, retarded or deferred) by virtue of the crystallization additive which, depending on its nature, permits a release of the active substance over periods which are two to twenty times longer than the same active substance packaged conventionally, for example in the form of tablets with immediate release. Thus, these pearls make possible a daily dose of the medications prepared using them, instead of the 2 or 3 daily doses with the conventional medication giving immediate release.

Among the crystallization additives which permit a delay effect there may be mentioned fatty acids, glycerol esters, hydrogenated oils, waxes and esterified polyoxyethylene glycols, no limitation being implied.

The apparatus will be described more completely with the aid of FIG. 1, attached hereto. The active substance exhibiting the supercooling phenomenon is introduced into the container 1 and the excipient in the container 2, or the molten mixture, excipient+active substance, is introduced into both containers. Both these containers are kept under an inert gas atmosphere. The molten liquids are delivered, by means of two tubes, above a nozzle which is kept in an atmosphere which is not cooled and which is even optionally heated (3). The nozzle has 1 to 24 or more perforations, preferably between 50 and 600 microns in diameter. The length of the perforation is preferably between 0.5 and 10 times its diameter.

This nozzle is subjected to a high frequency (500 to 10,000 hertz) electrical vibration system (4). The cold air which permits the active substance and the excipient to solidify is introduced at the bottom of the tower (5) and leaves below the nozzle (6) at a distance which is preferably approximately L/10 relative to the top of the tower, L being the height of the tower.

Each orifice of the nozzle is preferably in the shape of an inverted cone, the apex of the cone pointing towards the base of the tower, and this makes it possible to obtain a perfectly laminar flow of liquid.

The height of the tower varies between 1 meter and about ten meters; in the lower quarter of its height the tower may comprise a frustoconical perforated skirt (8) which centers the pearls into the fluidized bed.

The fluidized bed (7) which may be joined onto the bottom of the tower is, within the scope of the present invention, preferably a fluidized bed in the shape of a funnel provided at its base with a distribution grid making it possible to minimize adhesiveness to the walls and to promote wall-pearl impacts with the aim of increasing the rate of solidification. The addition of an apparatus of this type permits a more intense solidification of the mixture of constituents in the bead, the exterior being already solid as it enters the fluidized bed.

The beads or pearls obtained using the process of the present invention have a uniform shape and a diameter of between 0.1 mm and 1.5 mm. The quantity of active substance which is introduced varies from 5 to 95% by weight and preferably from 40 to 60% by weight.

These pearls can be processed into various pharmaceutical forms, such as sachets, gelatin capsules or tablets.

When they are being processed, it is sometimes useful to add flow aids, lubricants, inorganic fillers (talc, silicas, aluminium oxide) to avoid electrostatic phenomena, and sweeteners (saccharinate, aspartame) when packaging, for example in the form of sachets.

Before being formulated, the pearls may also be coated with a film-forming skin such as a gastroresistant coating based especially on cellulosic or acrylic resins and/or may be coated with a colored skin.

EXAMPLES

The present invention will be described more completely with the aid of the following examples, which should not be considered as limiting the invention.

The products which form part of the composition of the pearls are shown in Table 1.

The table shows:
the composition of the mixtures,
the operating conditions, i.e. the diameter of the holes,
the vibration frequency,
the nozzle temperature.

The surface velocities of the cooling air and of the fluidizing nitrogen are 1.5–1.8 m/s and 0.3–1 m/s respectively.

Procedure

The pairs are melted in a stirred reactor and then transferred into one or both pots.

The cooling air is introduced at the desired rate.

The fluidized bed is set in operation.

When the air exit temperature is in a steady state, the valve $V_1$ or $V_2$ allows nitrogen to enter at the chosen pressure and the liquid is transferred into the nozzle.

The frequency adjustment is performed by means of a generator, the pearls being observed visually with a stroboscope (if need be, the cooling air is drawn in through a bed of solid $CO_2$ so as to give it a temperature of 4° to 12° C. before entering the tower).

The pearls are recovered in the bottom of the tower; they exhibit a sufficient hardness for being processed into pharmaceutical form.

Photo

The attached photo shows the pearls obtained in Example 9, the scale between two parallel lines is 1 mm.

Dissolving test

The apparatus described in European Pharmacopoeia, 2nd edition V 5.4. (1986) and USP XXI (711) is employed.

Method of dissolving prilling:

100 mg or 200 mg test sample of ketoprofen, palette at 120 revolutions per minute,
media: 0.01N HCl 1 hour (8.6 ml HCl at 36% w/w q.s. 10 liters with $H_2O$) pH 4.5 2 hours 68 g of potassium dihydrogen phosphate q.s. 10 liters pH 6.6 16 hours Add x ml of 1N sodium hydroxide to the medium in order to obtain the desired pH:
x=8 ml for 500 ml of pH 4.5
x=16 ml for 1000 ml of pH 4.5
500 ml at 37° C. for the prills with 100-mg dosage
1000 ml at 37° C. for the prills with 200-mg dosage
Continuous reading at 260 nm with 1 mm cells.

$E_{1\ cm}^{1\%} = 657$ 0.01N HCl $E_{1\ cm}^{1\%} = 661$ pH 4.5

$E_{1\ cm}^{1\%} = 659$ pH 6.6

TABLE 1

| TESTS | PEARL COMPOSITION | | |
|---|---|---|---|
| | KETOPROFENE | PRECIROL | STEARIC ACID |
| 1 | 50 | 25 | 25 |
| 2 | 60 | 40 | — |
| 3 | 50 | 50 | — |
| 4 | 50 | 50 | — |
| 5 | 50 | 50 COMPRITOL | — |
| 6 | 50 | 10 | 40 |
| 7 | 70 | 10 | 20 |
| 8 | 60 | 25 | 15 |
| 9 | 67 | 13 CETYL ALCOHOL | 20 ETHYL CELLULOSE |
| 10 | 50 | 46.5 MAGNESIUM STEARATE | 3.5 STEARIC ACID |
| 11 | 60 MEPROBAMATE | 20 | 20 |
| 12 | 50 | | 50 |

| | OPERATING PROCEDURE | | | |
|---|---|---|---|---|
| TESTS | NOZZLE DIAMETER (mm) | FREQUENCY hertz | NOZZLE TEMPERATURE °C. | PEARL MEAN DIAMETER |
| 1 | 0.3 | 2880 | 95 | 600 μm |
| 2 | 0.3 | 3220 | 95 | 600 μm |
| 3 | 0.4 | 1400 | 95 | 800 μm |
| 4 | 0.3 | 4090 | 95 | 600 μm |
| 5 | 0.2 | 3580 | 100 | 450 μm |
| 6 | 0.4 | 800 | 91 | 800 μm |
| 7 | 0.4 | 700 | 91 | 900 μm |
| 8 | 0.4 | 1350 | 92 | 800 μm |
| 9 | 0.4 | 1225 | 92 | 750 μm |
| 10 | 0.3 | 900 | 90 | 600 μm |
| 11 | 0.4 | 800 | 101 | 800 μm |
| 12 | 0.4 | 2400 | 95 | 750 μm |

Although the invention has been described in conjunction with specific embodiments, it is evident that many alternatives and variations will be apparent to those skilled in the art in light of the foregoing description. Accordingly, the invention is intended to embrace all of the alternatives and variations that fall within the spirit and scope of the appended claims. The above references are hereby incorporated by reference.

We claim:

1. A process for the preparation of pearls based on a supercoolable active substance exhibiting delayed solidification upon being cooled and an indefinite crystallization point, comprising mixing a supercoolable active substance in molten form with an excipient promoting solidification and crystallization of the active substance, forcing the melt to pass through a nozzle which is subjected to a vibration, permitting the pearls formed to fall in a tower countercurrently to a gas, and collecting the pearls formed in the bottom of the tower.

2. A process according to claim 1, wherein the pearls have a size of 0.5 to 1.5 mm.

3. A process according to claim 1, wherein said nozzle is maintained at a temperature of about 90° C. to about 101° C.

4. The process according to claim 1, wherein the excipient promoting crystallization of the active substance is selected from fatty alcohols, fatty acids and their salts, glycerol esters, hydrogenated oils, polyols, waxes, polyethylene glycols and their esters.

5. The process according to claim 1, wherein the excipient is glycerol stearate or glycerol behenate.

6. The process according to claim 1, wherein a crystallization additive selected from inorganic oxides of silicon or titanium, phosphates, carbonates, talc and clays is added.

7. The process according to claim 1, wherein a surface-active agent is added.

8. The process according to claim 1, wherein the pearls are subsequently coated with a gastroresistant and/or coloring film-forming agent.

* * * * *